(12) United States Patent
Saiji

(10) Patent No.: US 6,878,832 B2
(45) Date of Patent: Apr. 12, 2005

(54) ISOLATION OF TAXANES

(76) Inventor: Lahu Saiji, 8119-29 Avenue, Apt. 203, Edmonton, Alberta (CA), T6K 3M7

( * ) Notice: Subject to any disclaimer, the term of this patent is extended or adjusted under 35 U.S.C. 154(b) by 0 days.

(21) Appl. No.: 10/416,776

(22) PCT Filed: Nov. 13, 2001

(86) PCT No.: PCT/CA01/01569
§ 371 (c)(1),
(2), (4) Date: Oct. 20, 2003

(87) PCT Pub. No.: WO02/38555
PCT Pub. Date: May 16, 2002

(65) Prior Publication Data
US 2004/0063977 A1 Apr. 1, 2004

Related U.S. Application Data
(60) Provisional application No. 60/248,302, filed on Nov. 13, 2000.

(51) Int. Cl.$^7$ .................................. C07D 305/14
(52) U.S. Cl. ............................ 549/510; 549/511
(58) Field of Search ........................ 549/510, 511

(56) References Cited
U.S. PATENT DOCUMENTS
5,969,165 A  10/1999  Liu

FOREIGN PATENT DOCUMENTS

| CA | 2094910 A1 | 5/1992 |
|---|---|---|
| CA | 2108265 A1 | 10/1992 |
| CA | 2126698 A1 | 6/1994 |
| CA | 2158050 A1 | 9/1994 |
| CA | 2210972 A1 | 6/1997 |
| CA | 2203844 A1 | 10/1998 |
| CA | 2213952 | 6/1999 |
| CA | 2258066 A1 | 7/2000 |

*Primary Examiner*—Ba K. Trinh
(74) *Attorney, Agent, or Firm*—John S. Child, Jr.

(57) ABSTRACT

An improved method for the isolation of taxanes of high purity from the crude extract of naturally occurring Taxus canadensis which comprises the steps of: a) filtering the crude extract by liquid column chromatography; b) enriching the taxanes obtained from step a) by precipitation and crystallization; and c) dissolving the taxanes extract in a polar organic solvent mixture comprising an alcohol and a non-alcohol solvent, which solution is then subjected to further separation by liquid column chromatography, and isolating substantially pure paclitaxel from cephalomannine; and all solvent mixtures used may be collected, purified and recycled without separation.

21 Claims, 3 Drawing Sheets

Continuing from Figure 1

Continued in Figure 3

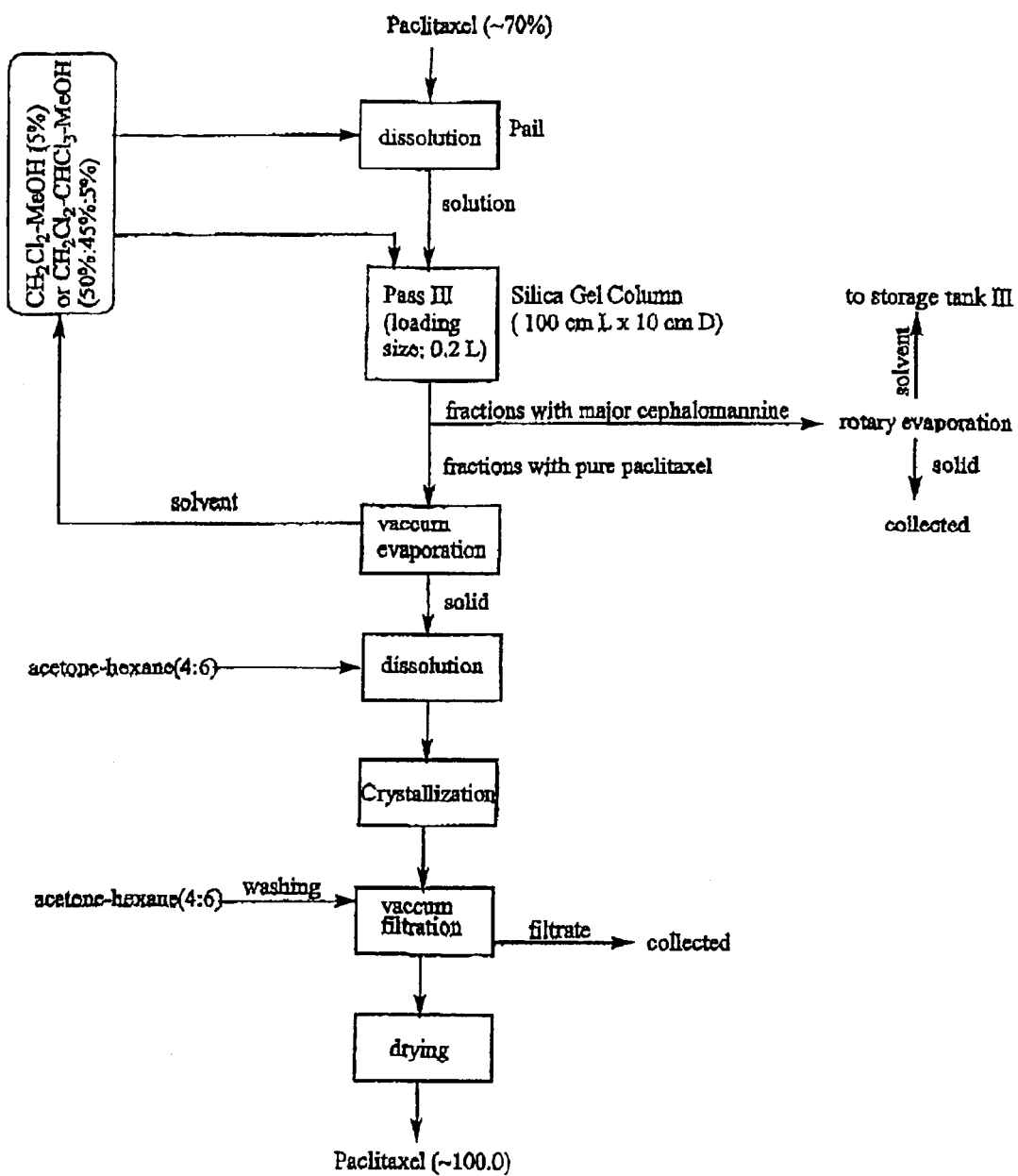
Figure 3
Continued from Figure 2

ISOLATION OF TAXANES

CROSS REFERENCE TO RELATED APPLICATIONS

This application claims the benefit under 35 U.S.C. §§ 120 and 371 and is a continuation of International Application No. PCT/CA01/01569, filed Nov. 13, 2001, which designates the United States of America and was published under PCT Article 21(2) in English as Published International Application No. WO 02/38555 A1 on May 16, 2002, and which is based on and claims priority under 35 U.S.C. § 119 to United States Provisional Application No. 60/248,302, filed Nov. 13, 2000. These International and Provisional Patent Applications are incorporated by reference in their entireties.

FIELD OF THE INVENTION

This invention relates to the isolation and production of taxanes from a crude extract of *Taxus canadensis* that is abundant in the eastern provinces of Canada. More particularly, the present invention relates to the chromatographic separation of substantially pure paclitaxel, cephalomannine, and 13-acetyl-9-dihydro-baccatin III (baccatin III) in high yields.

BACKGROUND OF THE INVENTION

Paclitaxel is an important active pharmaceutical Ingredient for chemotherapeutic treatment of metastatic cancers. The antitumor activity of paclitaxel is attributed to its interfering mitosis effect. Paclitaxel has been approved by the Federal Drug Agency in the U.S.A. and the Health Protection Branch of Health Canada for the treatment of ovarian cancers. The results of ongoing clinical trials for treatments on other cancers such as breast, lung and colon cancers are also promising.

Paclitaxel is a natural product originally isolated from the bark of the Pacific Yew tree (*Taxus brevifolia*), and it is also found in bark, needles, and twigs of many other Taxus species including *Taxus canadensis*. The concentration of paclitaxel in various plant materials is very low, less than 0.1%, which makes the process of isolating the compound from its natural sources very complex and challenging.

RELEVANT BACKGROUND ART

Chromatographic methods have been used for separating paclitaxel and related taxanes, as is provided by Eisohly et al in Canadian Patent Application No. 2,108,265 and by Nair in Canadian Patent Application No. 2,126,698. However, these methods are conducted on an analytical or laboratory preparative HPLC basis, both of which are fundamentally associated with low capacity and high cost. Therefore, they are essentially impractical for large-scale commercial production.

Some other methods have been developed for the separation of taxanes, including multi-step sedimentation, critical or near critical extraction, chemical modification and reverse phase chromatography.

In the multi-step sedimentation method of Canadian Patent No. 2,213,952 described by Zamir and Caron, the taxanes are dissolved in a polar organic solvent, then gradually added with a non-polar organic solvent to sedimentate. This method involves consuming large amounts of non-polar organic solvent that is difficult to recover, and therefore makes the production cost high.

In Canadian Patent Application No. 2,158,050 issued to Castor, critical or near critical extraction is applied to the separation of taxanes, but at the cost of expensive apparatus requirements.

To improve the yield of taxols, a chemical modification process for the separation of paclitaxel and cephalomannine was proposed by Pandey and Yankov in Canadian Patent Application No. 2,210,972. Cephalomannine is an analog of paclitaxel, which has a double bond group on its branch chain. In the method, cephalomannine is chemically converted to its bromine derivative, an irreversible change. The reaction must be performed in the absence of light, to avoid loss of reactive selectivity, but risking the possibility of damaging the paclitaxel. Furthermore, the chemical modification does not remove the requirement for the chromatographic separation step. This chemical modification makes the isolation process more costly and laborious.

Modified stationary phase methods include hydrocarbon-coated silica described by Rao in Canadian Patent Application No. 2,094,910 and polystyrene type resins described by Liu in Canadian Patent Application No. 2,258,066. These reverse phase HPLC based methods are effective on a laboratory scale, but are impractical for large quantity commercial production due to the high cost of the stationary phase and its low capacity, especially in those circumstances as where severe adsorptive contamination on the column occurs.

In Canadian Patent Application No. 2,203,844 issued to Liu there is described a method for isolating taxanes using dry column chromatography. The method involves the preparation of a crude extract of at least one Taxus species, wherein the crude extract is obtained by extraction with an aqueous alcoholic solvent. The following separation process needs a tedious preliminary solvent partition process, which involves the use of large amounts of volatile organic solvent. The solvents employed in the various steps of the process are not readily recycled for subsequent use, which adds significantly to the process cost.

Thus, the known techniques for the isolation and purification of paclitaxel from raw materials or crude extracts are currently limited or associated with laborious, non-economical and low-scale characteristics. There is therefore a need to provide a simpler, lower-cost, and more efficient method than is currently available for the isolation and purification of the valuable chemotherapeutic compound paclitaxel and related taxanes.

Thus there exists a need to provide a cost-effective method for producing substantially pure taxanes.

SUMMARY OF THE INVENTION

The present invention provides a process for the isolation and purification of paclitaxel from a crude extract that contains a mixture of taxane type compounds including paclitaxel, baccatin III and cephalomannine. The method comprises flash chromatographic passes of the crude sample on economical silica gel columns. These steps provide a refined and concentrated mixture of taxanes. The resulting mixture is then Isolated by a number of subsequent steps, selected from crystallization in alcohol, precipitation by a polar solvent, and fine separation of paclitaxel and cephalomannine by a specific binary solvent system. This allows the complete separation of taxanes without the need of chemical modification steps.

Further, all solvent mixtures may be collected and recycled without separation which allows the cost of producing the purified taxane to be reduced substantially. There are great costs with managing solvent wastes and the present process substantially reduces these costs.

More particularly, the present invention provides an improved method for the isolation of taxanes of high purity from the crude extract of naturally occurring *Taxus canadensis* which comprises the steps of:

a) filtering the crude extract by liquid column chromatography;

b) enriching the taxanes obtained from step a) by precipitation and crystallization;

c) separating the taxanes obtained from step a) by liquid column chromatography; and d) dissolving the separated taxanes in a polar organic solvent mixture comprising an alcohol and a non-alcohol solvent, which solution is then subjected to further separation by liquid column chromatography, and isolating substantially pure paclitaxel from cephalomannine;

and all solvent mixtures used may be collected, purified and recycled without separation.

DETAILED DESCRIPTION OF THE INVENTION

BRIEF DESCRIPTION OF THE DRAWINGS

In the accompanying drawings which are used to illustrate the invention,

FIGS. 1 to 3 are a flow chart which provides particular detail of the method of the invention.

Figure 1:
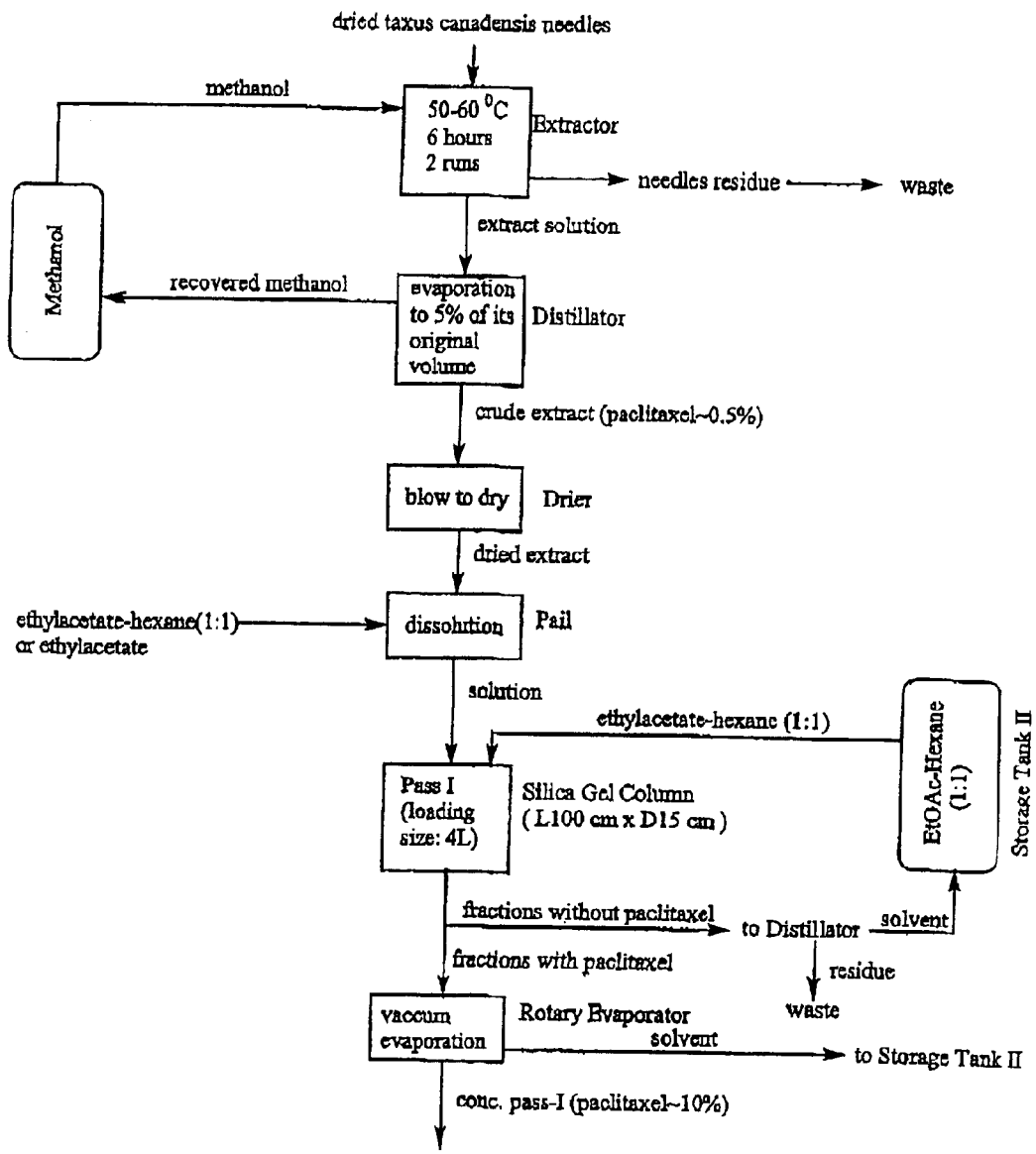
Figure 2:
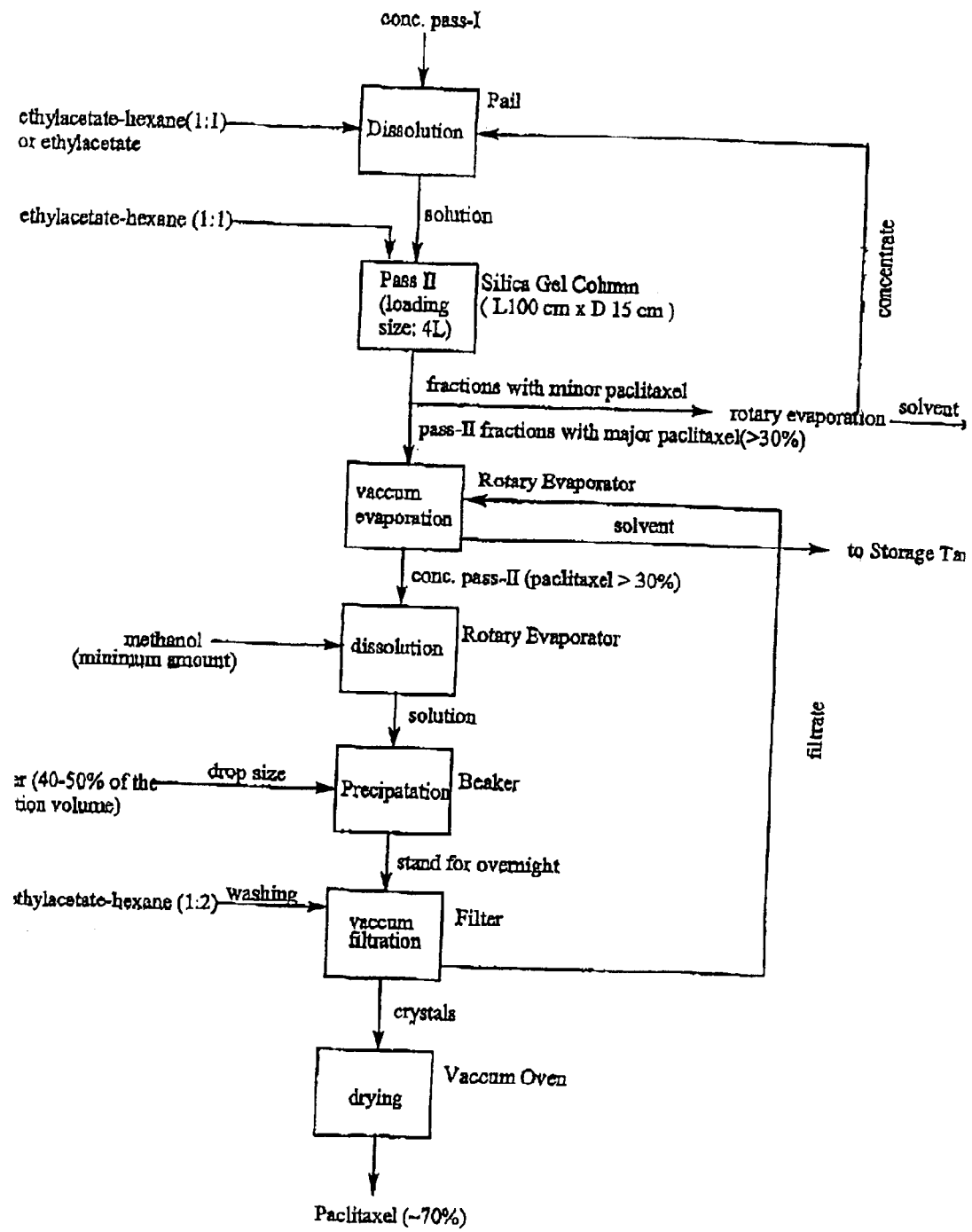

The flow chart of the method illustrated in FIGS. 1 to 3 provides an example of the method of the invention.

The present method starts with crude extract from plant material, such as barks, needles and twigs of the species *Taxus canadensis*, which is abundant in Eastern Canada. The young bark and new growth of needles and twigs that is two to three years is preferred. These plants grow up to four feet high in the Maritime Provinces of Canada and in Northern Quebec. The concentration of paclitaxel in the crude extract is approximately 0.6% w/w. by HPLC (high pressure liquid chromatography) analysis. The extraction process from other species is substantially similar. A typical method for obtaining the crude extract of *Taxus canadensis* is described hereafter. Dry plant material of *Taxus canadensis* is first ground well (by conventional means) and then is extracted with methanol under mechanical stirring at room temperature for 4 hours [Flow Chart shows 50–60° C. for 6 hours 2 runs]. The mixture is filtered and the filtrate is concentrated to 5% of its original volume by use of an industrial evaporator (Distillator) under vacuum to yield the crude extract. Other sources of crude extracts may also be used, as long as they are obtained from *Taxus canadensis*. It should be noted that plants grown in Canada are also found in Mexico, China and the U.S.A.

The so-obtained crude extract is dissolved in a polar organic solvent, preferably ethylacetate or ethylacetate-hexane (1:1). The direct loading of the crude extract onto a column should be avoided, since the high viscosity of the crude extract may simply clog the column. An industrial glass chromatographic column (15 cm×100 cm) is prepared by sealing one end with glass wool and setting it up vertically. A stationary phase of silica gel powder (1×250 mesh) is loaded in either dry powder or wet slurry form up to 70–80% of column height. Both dry powder and wet slurry packing are acceptable, as long as fresh or clean silica gel is used. The column height is not critical, but the particle size of silica gel powder should be such that a good flow through the column can be established. The homogenous solution of crude taxol extract is then loaded to the column. The recommended ratio of loading volume of the crude extract solution to the total packed column volume is 1:4–1:6 with the higher ratio being preferred. Although the best separation effect is reached at a ratio of the diameter to the length of column 1:6, the higher ratio of 1:4 is better to increase the amount of sample loading capacity. This also makes maximum use of the column for preliminary separation. After loading the crude extract solution, pressure is applied gently to the column so that the solution is fully loaded on the head of the silica gel layer. Now the column is ready for elution. Alumina of similar particle size may also be used as the stationary phase in the column, either as part or all of the phase.

The column is eluted with a mixture of ethylacetate-hexane (1:1 by v/v) under a pressure of about 25±5 psi. Other preferred ratios for this mixture include from 7:3 to 5:5, with 6:4 being preferred, also. A gradient elution technique may also be used, provided there is also a stable continuous solvent pumping system. In this case, the ratio of the mixture of ethylacetate-hexane starts at 2:8 and ends at 8:2. However, gradient elution is not recommended for an unstable discontinuous pumping operation, since it may reduce the separation effect with the tail components. The operation of column filtration is performed at a flow rate of 100–150 mL/min. The eluta is monitored and analyzed by TLC (thin liquid chromatography) or HPLC, and fractions containing taxanes are collected separately. It is also possible to monitor the taxane fractions by the chromatographic bands of the glass column for experienced operators. When the fraction containing taxanes is completely eluted out, which can be traced by TLC tests, the elution process is stopped. The collected fractions are concentrated by rotary evaporator around 50±5° C. under 25±10 mmHg vacuum. It has been reported in the literature that high temperature (e.g. >60° C.) may induce side-reactions of taxanes. The concentrated fraction contains approximately 10% paclitaxel. The column filtration process may be repeated once more, depending on the concentration of taxanes in the crude extract. Generally, the concentration of paclitaxel is enriched to about 30% after the second filtration.

After substantially removing all of the solvent by rotary evaporation, the enriched residue is dissolved in an alcohol solvent (methanol or ethanol) amounting to 3–5 times of its original volume. This solution is kept overnight. 9-Dihydro-13-acetyl-baccatin III is then precipitated as crystals and filtered from the alcohol solution. The purity of 9-dihydro-13-acetyl-baccatin III crystals is about 90%, which can easily be further purified by recrystallization.

To the alcohol solution of taxanes, there is further added drop wize, deionized or distilled water to about 40% of its original volume. This operation is preferably performed under mechanical or magnetic stirring. The resulting solution is kept overnight. The so-formed precipitate is filtered and washed by a mixture of ethylacetate-hexane (1:2 v/v). This solid essentially is a mixture of paclitaxel (~70%), cephalomannine (25%), and a small amount other, taxanes (5%) based on HPLC analyses.

To separate paclitaxel with cephalomannine, the traditional method involves the use of chemical modification reaction, which has been discussed previously. In the present method, the solid mixture is dissolved in a polar organic solvent, for example methylene chloride, and then loaded onto a silica gel column (100 cm×10 cm). The ratio of loading volume to column volume is at most 1:10–1:20. The chromatographic column is eluted with a mixture of an alcohol solvent and a polar organic solvent. This specific binary solvent system is composed of an alcohol solvent (chosen from methanol, ethanol, or iso-propanol) and a non-alcohol solvent (chosen from chloroform, dichloromethane, xylene, or toluene). For example, a mixture of methanol (5%) and methylene chloride (95%) has been found to be suitable. The eluta is analyzed and monitored with TLC or HPLC. Fractions of paclitaxel and cephalomannine are collected separately. The separation is achieved in a simple and straightforward way, as a result of the use of an appropriate binary solvent. The collected fractions of taxanes are further purified by recrystallization in a mixture of acetone-hexane (4:6) solution so as to obtain pure compounds. The so-obtained crystals are dried under vacuum in an oven at 50° C. overnight. The purity of the compounds is ~100.00% for paclitaxel and ~99% for cephalomannine based on HPLC data.

It will be apparent that the solvent mixtures may all be collected for recycling without separation into individual solvents, an aspect of the present method that is possible because of the binary solvent mixtures employed.

The following example further illustrates the present invention. This process can be scaled up readily to commercial scale using this example as a guide.

EXAMPLE

All chemicals were used as received from the manufacturer or supplier, and analyzed before use. Glass chromatographic columns and silica gel were obtained from Fareast Pharmaceutical Equipments Inc. China. Industrial solvents were obtained from Stanchen, Canada. HPLC reference chemicals such as paclitaxel, cephalomannine, and 9-dihydro-13-acetyl-baccatin III were obtained from Hauser, USA. Fluorescent silica gel TLC plates were obtained from Waters, USA. Dionex 500 HPLC system was used for analyzing the components in the process.

A crud extract (0.5 kg) obtained from needles of *Taxus canadensis* was dissolved in 4 L of ethylacetate. The solution then was loaded on an industrial glass chromatographic column (15 cm×100 cm) which was already packed with silica gel powder (1×250 mesh) to 70% of the column height. The column was eluted with ethylacetate-hexane (1:1 v/v) under a pressure of 25±5 psi. The flow rate was controlled to be about 100~150 mL/min.

The fractions containing taxanes were monitored by TLC and collected together, and in total, amounted to 15 litres. After concentration by rotary evaporation under vacuum (50±5° C., 15~25 mmHg), the residue obtained upon first-pass was re-dissolved in ethylacetate again and then subjected to a second-pass of the chromatography separation, followed by drying by rotary evaporation. The enriched residue of taxanes so obtained was dissolved in methanol (200 mL) and kept at room temperature overnight to yield crystals of 13-acetyl-9-dihydro-baccatinIII (15 gram).

To the methanol solution of taxanes, distilled water (~40% of the volume) was added while under vigorously stirring. The solution then was kept at room temperature overnight. The so-formed precipitate (5 g, ~70% paclitaxel, ~25% cephalomannine, ~5% impurities) was filtered.

The obtained mixture of taxanes was dissolved in 50 mL of methylene chloride and then loaded on a silica gel column (10 cm×100 cm). The column was eluted by a mixture of methanol (5%) and methylene chloride. The fractions were analyzed by TLC or HPLC. Fractions containing paclitaxel and cephalomannine were collected separately. After removing the solvent by rotary evaporation, the separated paclitaxel and cephalomannine were further recrystallized in a mixture of pure acetone-hexane (4:6 v/v) to give the desired paclitaxel (3 g, ~100%) and cephalomannine (1 g, ~99%) as white needle-like crystals.

The invention may be varied in any number of ways as would be apparent to a person skilled in the art and all obvious equivalents and the like are meant to fall within the scope of this description and claims. The description is meant to serve as a guide to interpret the claims and not to limit them unnecessarily.

What is claimed is:

1. An improved method for the isolation of taxanes of high purity from crude extract of naturally occurring *Taxus canadensis* which comprises the steps of:
    a) filtering the crude extract by liquid column chromatography to provide a taxanes extract;
    b) enriching the taxanes extract obtained from step a) by precipitation and crystallization;
    c) dissolving the separate taxanes extract obtained from step b) in a polar organic solvent mixture comprising an alcohol and a non-alcohol solvent, which solution is then subjected to further separation by liquid column chromatography, and isolating substantially pure paclitaxel from cephalomannine;

and all solvent mixtures used may be collected, purified and recycled without separation.

2. The method according to claim 1, wherein the filtration of crude extract (a) is at least one column passing.

3. The method according to claim 2, wherein the column passing is conducted under a pressure of about 25±5 psi. at a flow rate of from about 100 to about 150 ml/mm.

4. The method according to claim 2, wherein said column passing comprises the additional steps of loading crude extract to a packed chromatographic column, eluting the column by an organic solvent, collecting the fractions containing taxanes, and concentrating the fractions.

5. The method according to claim 4, wherein said chromatographic column is an industrial glass column (15 cm×100 cm) packed with 1×250 mesh dry silica gel particles.

6. The method according to claim 4, wherein said organic solvent is a mixture of ethylacetate and hexane with a volume ratio of from about 5:5 to about 7:3.

7. The method according to claim 4, wherein said concentration of fractions is by rotary evaporation below about 50° C. under reduced pressure.

8. The method according to claim 1, wherein said precipitation and crystallization (b) additionally comprises the steps of making an alcohol solution of taxanes, adding a polar solvent to the alcohol solution of taxanes, leaving the solution to stand for overnight, filtering the precipitate, and washing the crystals.

9. The method according to claim 8, wherein said alcohol solution of taxanes is a solution of methanol or ethanol.

10. The method according to claim 8, wherein said polar solvent is deionized or distilled water.

11. The method according to claim 8, wherein said washing of crystals is conducted with ethylacetate-hexane (1:2).

12. The method according to claim 11, wherein said separation of the taxanes (c) additionally comprises the steps of loading a solution of the washed crystals on a chromatographic column, eluting the column with a binary organic solvent system, collecting the fractions with paclitaxel, cephalomannine, and 13-acetyl-9-dihydro-baccatin III separately, concentrating the fractions, recrystallizing the taxanes, and drying the crystals.

13. The method according to claim 12, wherein said chromatographic column is an industrial glass column (10 cm×100 cm) packed with 1×250 mesh dry silica gel particles.

14. The method according to claim 12, wherein said binary organic solvent system is composed of an alcohol solvent and a non-alcohol solvent.

15. The method according to claim 14, wherein said binary organic solvent system has a volume ratio of alcohol solvent to non-alcohol solvent of from about 2:98 to about 10:90.

16. The method according to claim 14, wherein said alcohol solvent is an organic solvent selected from the group comprising methanol, ethanol, and isopropanol.

17. The method according to claim 16, wherein said non-alcohol solvent is an organic solvent selected from the group comprising chloroform, methylene chloride, toluene and xylene.

18. The method according to claim 12, wherein the concentration of fractions is conducted on a rotary evaporator below about 50° C. under reduced pressure of about 25 mmHg.

19. The method according to claim 12, wherein said recrystallization of taxanes is conducted in a mixture of acetone and hexane with a volume ratio of about 2:3.

20. The method according to claim 12, wherein said crystal drying is conducted in a vacuum oven at about 50° C. under about 10 cmHg.

21. An improved method for the isolation of taxanes of high purity from a crude extract of naturally occurring *Taxus canadensis* which comprises the steps of:

a) filtering the crude extract by liquid column chromatography to provide a taxanes extract;

b) enriching the taxanes extract obtained from step a) by precipitation and crystallization;

c) separating the taxanes extract obtained from step b) by liquid column chromatography to provide separated taxanes; and d) dissolving the separated taxanes obtained from step c) in a polar organic solvent mixture comprising an alcohol and a non-alcohol solvent, which solution is then subjected to further separation by liquid column chromatography, and isolating substantially pure paclitaxel from cephalomannine;

and all solvent mixtures used may be collected, purified and recycled without separation.

* * * * *